United States Patent [19]

Kitchens

[11] 4,144,152
[45] Mar. 13, 1979

[54] DEHALOGENATION OF HALOGENATED COMPOUNDS

[75] Inventor: Judith A. F. Kitchens, Haymarket, Va.

[73] Assignee: Atlantic Research Corporation, Alexandria, Va.

[21] Appl. No.: 890,871

[22] Filed: Mar. 27, 1978

[51] Int. Cl.$^2$ .............................................. B01J 1/10
[52] U.S. Cl. ................................. 204/158 R; 250/527
[58] Field of Search .................................... 204/158 R

[56] References Cited

U.S. PATENT DOCUMENTS 3,977,952  8/1976  Knoevenagel et al. ......... 204/158 R

OTHER PUBLICATIONS

Ruzo et al., JACS, vol. 96 (12), 1974, pp. 3809–3813.
Sawai et al., Kogai, vol. 8(2), 1973, pp. 49–57.
Ellis et al., The Chem. Action of Ultraviolet Rays, (1941), pp. 314–315.

*Primary Examiner*—Howard S. Williams
*Attorney, Agent, or Firm*—Martha L. Ross

[57] ABSTRACT

Process for degrading halogenated organic compound having C-halogen groups to remove halogen atoms from said compound by treating it with ultraviolet (UV) radiation and hydrogen. Process for degrading such compound by treating it in aqueous alkaline solution with UV radiation.

112 Claims, 10 Drawing Figures

DEHALOGENATION OF HALOGENATED COMPOUNDS

BACKGROUND

Many halogenated compounds are employed for a variety of practical uses, e.g., as pesticides, soil fumigants, solvents, etc.. Many escape into the environment, as for example in manufacturing or application wastes and spills. Some, such as pesticides, are applied in such a manner as to become part of the environment. It has been found that a number of such compounds, particularly though not necessarily polyhalogenated compounds, are toxic to plant and animal life. Although some of the compounds are bio- and/or photo-degradable so that they soon disappear from the environment, a substantial number are resistant to environmental degradation and remain in poisonous form for periods as long as many months or years. As a result, a good deal of research has been done to find reliable and economical treatment methods to degrade such compounds into environmentally safe products.

Some work has been done with treatment of certain halogenated compounds variously with UV radiation or with UV radiation and oxygen, air or ozone. To inventor's knowledge, there have been no prior teachings of the use of a chemical reduction treatment employing UV and hydrogen free from any added oxidizer, such as air or oxygen per se, or the use of UV alone in which the compound is in aqueous alkaline solutions. U.S. Pat. No. 3,977,952 teaches the required use of oxygen (or air) plus UV, preferably in the presence of HCl catalyst. In column 1, the patent mentions the use of carbon dioxide, water vapor, air or hydrogen as carrier gases for gas phase reaction. The reference to hydrogen appears to be inadvertent since no one skilled in the art would use hydrogen within the context of an oxygen oxidation process. The hydrogen would oxidize to water and present a serious hazard of explosion.

DRAWINGS

SUMMARY

Figure 1:
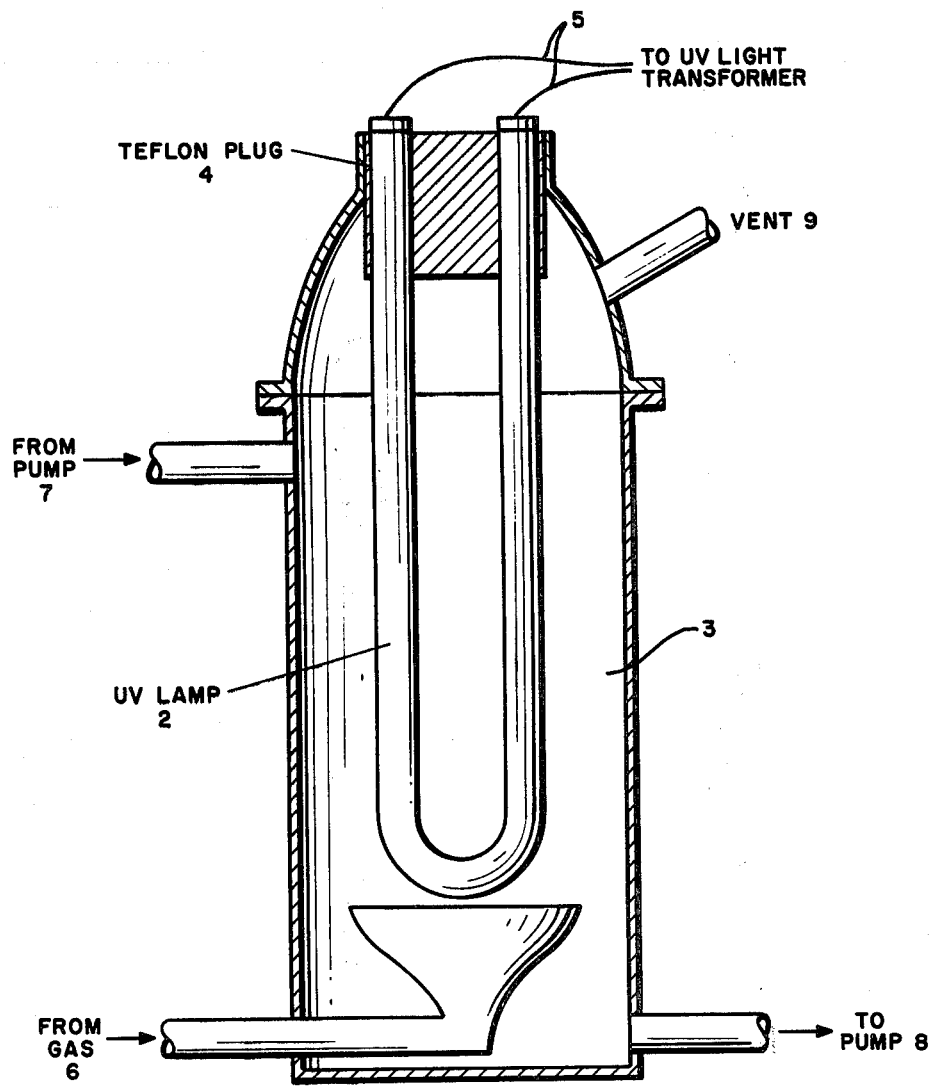
FIG. 1 is a schematic drawing of apparatus used in the process.

The treatment of a halogenated organic compound having at least one C-halogen group with UV radiation and hydrogen in the absence of any substantial amount of oxidizing agent reduces the compound by breaking the carbon-halogen linkage and producing halogen ions, thereby at least partially dehalogenating the compound (in the case of a polyhalogenated compound). The treatment may also result in further degradation of the at least partially dehalogenated compound. The process may be employed with monohalogenated compounds, but will more generally be used to treat polyhalogenated compounds because of their generally greater toxicity and resistance to environmental degradation.

The process can be used generally as a means for dehalogenation and is particularly useful in the treatment of contaminated effluent wastes from manufacturing processes or from contaminated water, soil, sludges or other wastes already present in the environment.

The dehalogenation mechanisms which occur in the process are generic in nature. They are operative regardless of the structure of the compound or the presence of other substituents or molecular components, such as oxygen, sulfur, nitrogen, metals or the like. The effect of these variable manifestations is primarily in the energy of the C-halogen bond and can be compensated for by employing higher or lower energy UV radiation within the stated range. The halogen substituents can include chlorine, bromine, fluorine, and iodine. The different C-halogen groups generally differ in bond energy. C-F groups, for example, generally have particularly high bond energies as compared with the other C-halogen groups and require more energetic UV wavelengths in the dehalogenation process.

Examples of compounds which are particularly suitable for treatment by the UV plus $H_2$ process of the invention because of their demonstrated or potential toxicity include but are not limited to kepone (and its gemdiol) decachloropentacyclo($5.3.0.0^{2,6}.0^{3,9}.0^{4,8}$.)decan-5-one; halogenated biphenyls; halogenated cyclodienes, such as aldrin, dieldrin, and hexachlorocyclopentadienes; dibromochloropropane; halogenated phthatlic anhydrides, such as polybromophthalic anhydride; tetrachloroethylene; polychlorodioxins such as tetrachlorodibenzodioxin; halogenated organic phosphates, such as 2,2-dichlorovinyldimethyl phosphate (Dichlorvos).

The process can be employed in gaseous phase where the halogenated organic compound is gaseous or in the form of a finely divided liquid or solid. In such case, the hydrogen acts as diluent, carrier, and reactant. Where the compound is in liquid or solid form, it is generally desirable to dissolve it in a suitable solvent which preferably is substantially transparent to the particular UV wavelengths. Use of a solvent is particularly advantageous where the compound is a contaminant which must be separated from other materials, such as sludge or mud.

The particular solvent used is determined by the solubility characteristics of the particular halogenated compound. It can be, for example, water, methanol, ethanol, 1- and 2-propanol, hexane, cyclohexane, acetonitrile, and preferably their alkaline solutions.

An aqueous alkaline solution, where alkalinity is preferably produced by the presence of alkali metal ions and preferably by means of an alkali metal oxide or hydroxide (to minimize potentially obstructive anions), such as sodium or potassium oxides and hydroxides, is particularly useful in the case of halogenated organic compounds which have substituents that react to produce soluble alkali metal salts. Examples include but are not limited to kepone (which normally hydrolyzes to the gem-diol in the presence of water or atmospheric moisture); aryl compounds having aryl-OH substituents, e.g., phenol-type compounds; diol-type compounds; carboxylic acids; anhydrides, such as phthalic anhydride-type compounds; sulfonic acids; and the like.

Compounds which are not soluble in aqueous alkaline solutions can generally be adequately solubilized by means of a suitable organic solvent. Preferably, though not essentially, the organic solvent is rendered alkaline, e.g., by addition of an alkali metal oxide or hydroxide, since it has been found that an alkaline pH can result in more rapid and greater degradation. Methanol is a preferred solvent because of its good solubilizing capability, its good UV transmission properties, and its relatively low cost which is of particular importance in the case of large scale application.

The UV radiation, as aforementioned, should be in the range of about 1800 to 4000Å. Preferably, it is in the shorter wavelength portion of this range, namely up to about 2537Å. Wavelengths of about 2537Å and 1850Å are particularly preferred because of the generally high absorptivity of halogenated organic compounds of these wavelengths.

The hydrogen input, quantitatively, should be sufficient, during the time of the treating procedure, to be in stoichiometric equivalency to the number of halogen atoms to be removed, or in excess thereto. In the case of liquid phase solvent treatment, the effective limiting value is the saturation concentration of the hydrogen in solution. Continued input of hydrogen to maintain saturation provides the optimum amount.

The process can be carried out at ambient temperature in relatively simple apparatus. The halogenated organic compound should receive maximum exposure to the UV radiation. This can be accomplished by such state-of-the-art expedients as minimizing the distance that the radiation needs to travel to or through the treatment volume; recirculation of the treatment medium; turbulene-creating means such as baffles or rotors; and the like. The process can be designed for batch or continuous treatment.

It has also been found that substantial degradation can be obtained by treatment of the halogenated compound in aqueous alkaline solution by treatment with UV radiation within the stated broad and preferred ranges of wavelength. Such treatment is limited to compounds, as aforedescribed, which are soluble in aqueous alkaline solution without requiring additional use of an organic solvent. In all other respects, the aforediscussion of various aspects of the process and generic application regardless of compound structure and substituents are applicable to such process using UV radiation alone.

DETAILED DESCRIPTION

FIG. 1 shows a schematic drawing of a reactor as employed in experimental evaluation. U-shaped UV tube 2 is positioned longitudinally in reactor chamber 3, and is held in air-tight position by Teflon plug 4, and is connected by wires 5 to a transformer (not shown). Hydrogen gas is pumped in via inlet tube 6. Reaction solution is pumped in via inlet tube 7 and is continuously recirculated by a pump (not shown) via outlet tube 8. Vent 9 provides for the exit of volatiles.

As used in the experiments below, the reactor diameter was 4 inches. Capacity was 1.5 l. The lamp size was 15¼ inches in overall length with an arc length of 24½ inches and tube diameter of 11/16 inch. Lamp input was 30W and output intensity was 10.4W. UV wavelength was 2537Å.

EXAMPLE 1

Kepone Treatment

Kepone, which has been used as an insecticide, has posed formidable problems because of its great toxicity and resistance to bio- and photo-degradation in the environment. It is highly toxic to normally-occurring degrading microorganisms. Although it can undergo some photodecomposition when exposed to sunlight to the dihydro compound (leaving a compound having 8 Cl substituents), this degradation product does not significantly reduce toxicity.

Kepone was made up into three different stock solutions:

a. 212ppm in methanol; solution pH6.

b. 237ppm in methanol alkalized to pH10 with NaOH.

c. 230ppm in water containing 5% NaOH.

1.5 l quantities of the kepone stock solutions were variously treated in the apparatus aforedescribed (UV λ = 2537Å) with UV alone, UV plus $O_3$ at an ozone flow rate of 0.41 l/min. and UV plus $H_2$ at a hydrogen flow rate of 0.75 l/min.

Samples were prepared for quantitative gas chromatographic analysis in the following manner.

1. Measured volumes of the samples were neutralized with ULTREX (Cl-free) nitric acid, if basic.

2. The samples were evaporated to dryness.

3. The dried sample was diluted to 100 ml with 6% methanol in benzene.

The resulting solutions were analyzed on a Hewlett-Packard 5750 with electron capture detector. The following conditions were used:

injection port temperature — 300° C.
detector temperature — 300° C.
oven temperature — 250° C.
gas flow — 50 ml/min Ar/$CH_4$
column — 10% DC 200 on Chromosorb HP 100/200

The aqueous NaOH solutions were analyzed on a Hewlett-Packard 3880 using the following conditions:

injection port temperature — 200° C.
oven temperature — 180° C.
gas flow — 45 ml/min AR/$CH_4$
column — 5% OV-210 on 100/120 GCQ Chloride ion concentration was also determined on all of the samples. An Orion solid state chloride ion electrode was used for this purpose. Samples in methanol were prepared by neutralizing 5 ml of the sample with ULTREX nitric acid. Following evaporation to dryness, the samples were dissolved in 8 ml of distilled water. In the case of aqueous sodium hydroxide solutions, 10 ml samples were neutralized with ULTREX nitric acid before the analyses. Chloride ion concentrations were determined by comparison to standard curves generated from sodium chloride standards containing equal amounts of sodium nitrate as the samples.

During the course of the experimental runs, samples were taken at 15, 30, 60, 90 and 120 min. (+180 min for aqueous NaOH solution treated with UV plus $H_2$) to determine rate of degradation with time.

Table I gives the results obtained in terms of the remaining concentration of kepone at the end of the indicated time period and the percent degradation.

TABLE I

| Initial Conc. ppm | Sample Conditions | Treatment Conditions | | Final Conc. | % Degradation |
|---|---|---|---|---|---|
| | | Gas | Time | | |
| 212 | Methanol pH 6 | 2537Å Hydrogen | 120 min. | 177 ppm | 16.5% |
| 237 | Methanol pH 10 | 2537Å | 120 min. | 155 ppm | 34.6% |
| 237 | Methanol pH 10 | 2537Å Ozone | 110 min. | 190 ppm | 19.8% |
| 237 | Methanol pH 10 | 2537Å Hydrogen | 120 min. | 115 ppm | 51.5% |
| 230 | 5% Ag.NaOH Sol. pH > 14 | 2537Å | 120 min. | 140 ppm | 39.1% |
| 230 | 5% Ag.NaOH Sol. pH > 14 | 2537Å Ozone | 120 min. | 181 ppm | 21.3% |
| 230 | 5% Ag.NaOH Sol. pH > 14 | 2537Å Hydrogen | 120 min. | 37 ppm | 83.9% |
| 230 | 5% Ag.NaOH Sol. pH > 14 | 2537Å Hydrogen | 180 min. | 12 ppm | 94.8% |

Figure 2:
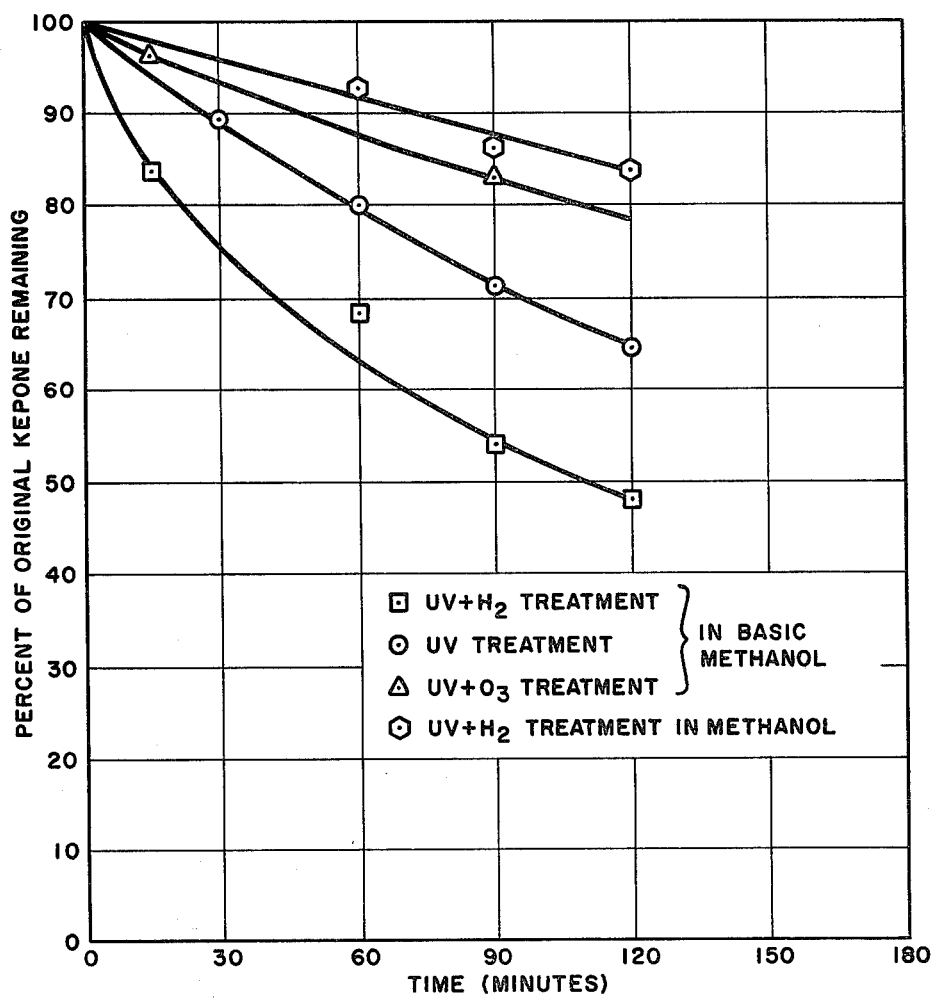
FIG. 2 shows comparative percent degradation of kepone in methanol solution with treatment by UV plus $H_2$ and in alkaline methanol solution with treatment by UV alone, UV plus $O_3$ and UV plus $H_2$.

Table I and FIG. 2 show the substantially higher % degradation at two hours by the basic methanol treatment with UV plus $H_2$ as compared with the other treatment methodologies. They also indicate that, although the UV plus $H_2$ treatment with non-alkalized methanol (pH 6) gives appreciable reduction, the alkaline methanol gives very considerably improved results. FIG. 2 also shows the considerably higher rate of reduction by the UV plus $H_2$ treatment.

Figure 3:
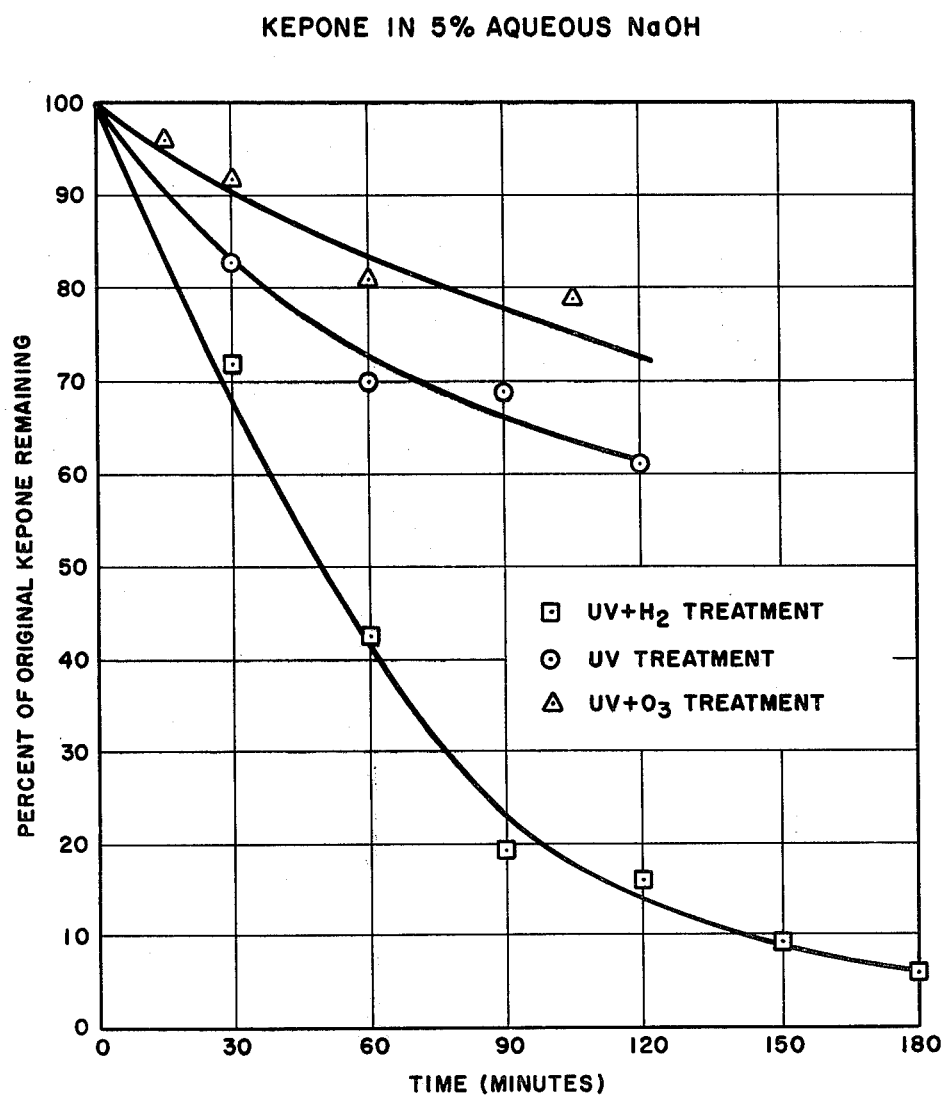
FIG. 3 shows the comparative percent degradation of kepone in aqueous alkaline solution by UV alone, UV plus $O_3$ and UV plus $H_2$.
Figure 4:
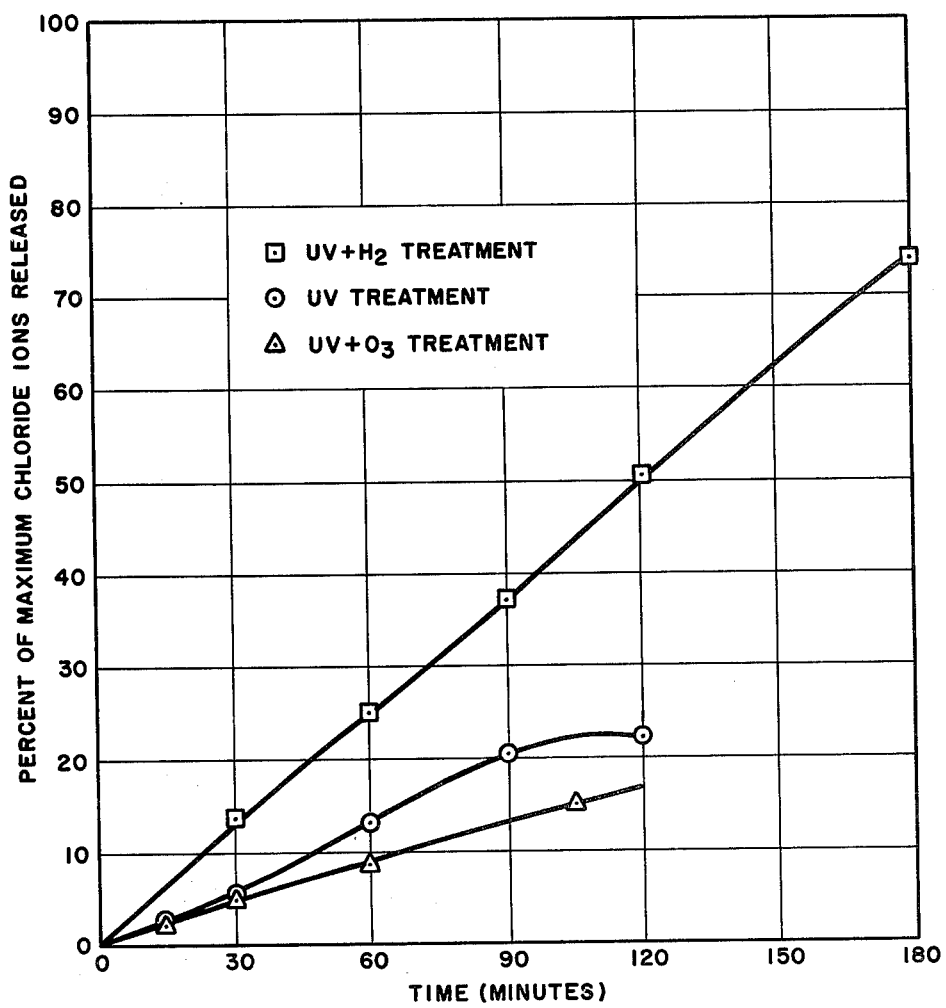
FIG. 4 shows the comparative percent of maximum chloride ions released from kepone in aqueous alkaline solution by treatment with the three methods.

Table I and FIG. 3 show the very substantially higher rate and percent degradation produced by the UV plus $H_2$ treatment in aqueous NaOH as compared with the UV alone and UV plus $O_3$ treatments. At the end of 3 hours, the UV plus $H_2$ treatment almost completely removes the kepone. These degradation results are substantially verified by FIG. 4 which shows the percent of free Cl ions released as a function of time for the UV alone, UV plus $O_3$, and UV plus $H_2$ treatments. After 3 hours only about 26.5% of the chlorine appears to remain in C-Cl group combination in chlorine-degraded products. At 120 minutes about 50.5% of the chlorine has been transformed into free ions by UV plus $H_2$, about 23% (less than one-half) and UV, and only about 16.5% by UV plus $O_3$. These results indicate that as many as 6 to 8 chlorine atoms are removed from the kepone molecules by the UV plus $H_2$ treatment.

It should be noted that although the results obtained with UV alone in aqueous alkaline solution are not as good as those produced by the UV plus $H_2$ treatment, substantial degradation is obtained, so that this treatment can be useful in the case of halogenated organic compounds which are substantially soluble in aqueous alkaline solution as aforedescribed.

EXAMPLE 2

Treatment of Polychlorinated biphenyl (PCB)

Aroclor 1254 is a mixture of the higher chlorinated biphenyls containing 54% chlorine by weight (an average of 4.96 chlorine atoms per molecule). A typical analysis of Aroclor 1254 is presented in Table II (Versar Inc., 1976).

TABLE II

| Empirical Formula | Molecular Weight | No. of Chlorine per Biphenyl | Wt. % Chlorine | No. of Isomer | Weight % |
|---|---|---|---|---|---|
| $C_{12}H_{10}$ | 154 | 0 | 0 | 1 | <0.1 |
| $C_{12}H_9Cl$ | 188 | 1 | 18.6 | 3 | <0.1 |
| $C_{12}H_8Cl_2$ | 222 | 2 | 31.5 | 12 | <0.5 |
| $C_{12}H_7Cl_3$ | 256 | 3 | 41.0 | 24 | 1 |
| $C_{12}H_6Cl_4$ | 290 | 4 | 48.3 | 42 | 21 |
| $C_{12}H_5Cl_5$ | 324 | 5 | 54.0 | 46 | 48 |
| $C_{12}H_4Cl_6$ | 358 | 6 | 58.7 | 42 | 23 |
| $C_{12}H_3Cl_7$ | 392 | 7 | 62.5 | 24 | 6 |
| $C_{12}H_2Cl_8$ | 426 | 8 | 65.7 | 12 | <0.01 |

Aroclor 1254 is slightly soluble in water, having an overall solubility of $1.2 \times 10^{-2}$ mg/l. Solubility of the various components varies from 0.0088 mg/l for the hexachlorobiphenyls to 5.9 mg/l for the monochlorobiphenyls. The vapor pressure for the 1254 mixture is $7.71 \times 10^{-5}$ mm Hg. Theoretical half-life from a 1-meter water column has been calculated as 1.2 minutes. Thus Aroclor 1254, like many other slightly soluble chlorinated compounds, is readily vaporized from the surface of water. Such vaporized compound could, therefore, escape degradation treatment.

Aroclor 1254 was dissolved in methanol alkalized to pH 11 with NaOH to make a 10.92 ppm stock solution. 1.5 l portions of this stock solution were treated with UV alone, UV plus ozone at an ozone flow rate of 0.41 l/min., UV plus hydrogen at a hydrogen flow rate of 0.75 l/min. for 120 minutes each in the reactor aforedescribed. Samples of ~8 ml each were taken every 15 minutes. Analyses were performed on the 15-, 30-, 60-, 90-, and 120-minute samples.

Quantitative analyses for the PCBs were performed on a Hewlett-Packard 3880 gas chromatograph with an EC-$Ni^{63}$ electron capture detector. G.C. conditions were as follows:

injection port temperature — 200° C.
detector temperature — 300° C.
oven temperature — 220° C.
gas flow — 50 ml/min Ar/$CH_4$
Column — 15% OV-17, 1.95% QF-1 on 100/120 GCQ The samples were prepared for analysis by neutralizing a known volume with ULTREX nitric acid, followed by evaporation of the solution to dryness at room temperature. The samples were brought up to 10 ml with pesticide grade hexane. Stock solutions were treated in the same manner to ensure that there was no loss from evaporation.

Areas under the individual peaks were measured with an electronic integrator and compared to standard curves to determine the concentration. Peaks 1-9 in the chromatogram were monitored individually as well as the total area under peaks 1-9. No attempt was made to identify the individual components.

Figure 5:
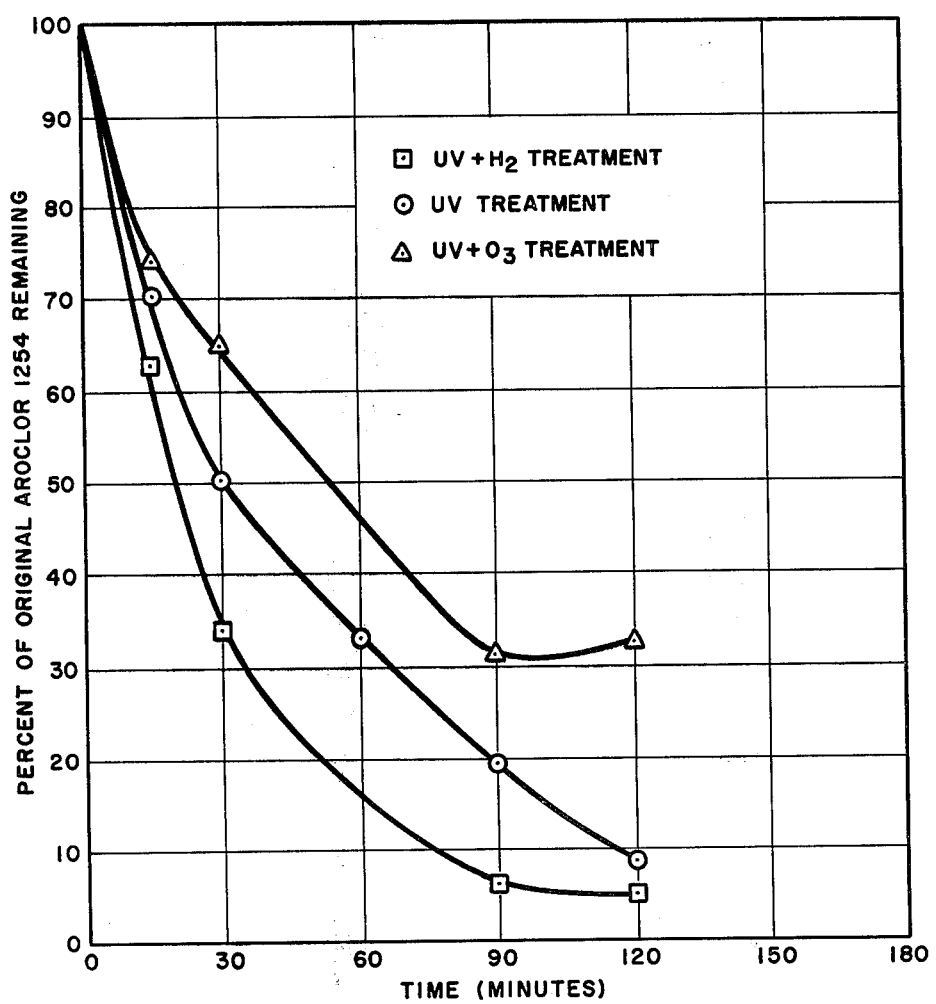
FIG. 5 shows the comparative total percent degradation of Aroclor 1254 in basic methanol by UV alone, UV plus $O_3$, and UV plus $H_2$.

The results of the G.C. analyses of the Aroclor 1254 degradation samples are presented in FIGS. 5-8. FIG. 5 shows the total concentration of chlorinated biphenyls remaining as a function of time for the three treatment methodologies. As indicated in this figure, the UV plus $H_2$ treatment is more effective than either UV alone or UV plus $O_3$. The initial rate for the UV plus $H_2$ treatment is significantly faster than the other treatment methodologies even though the final amount degraded for the UV alone and the UV plus $H_2$ after 2 hours is approximately the same.

Figure 6:
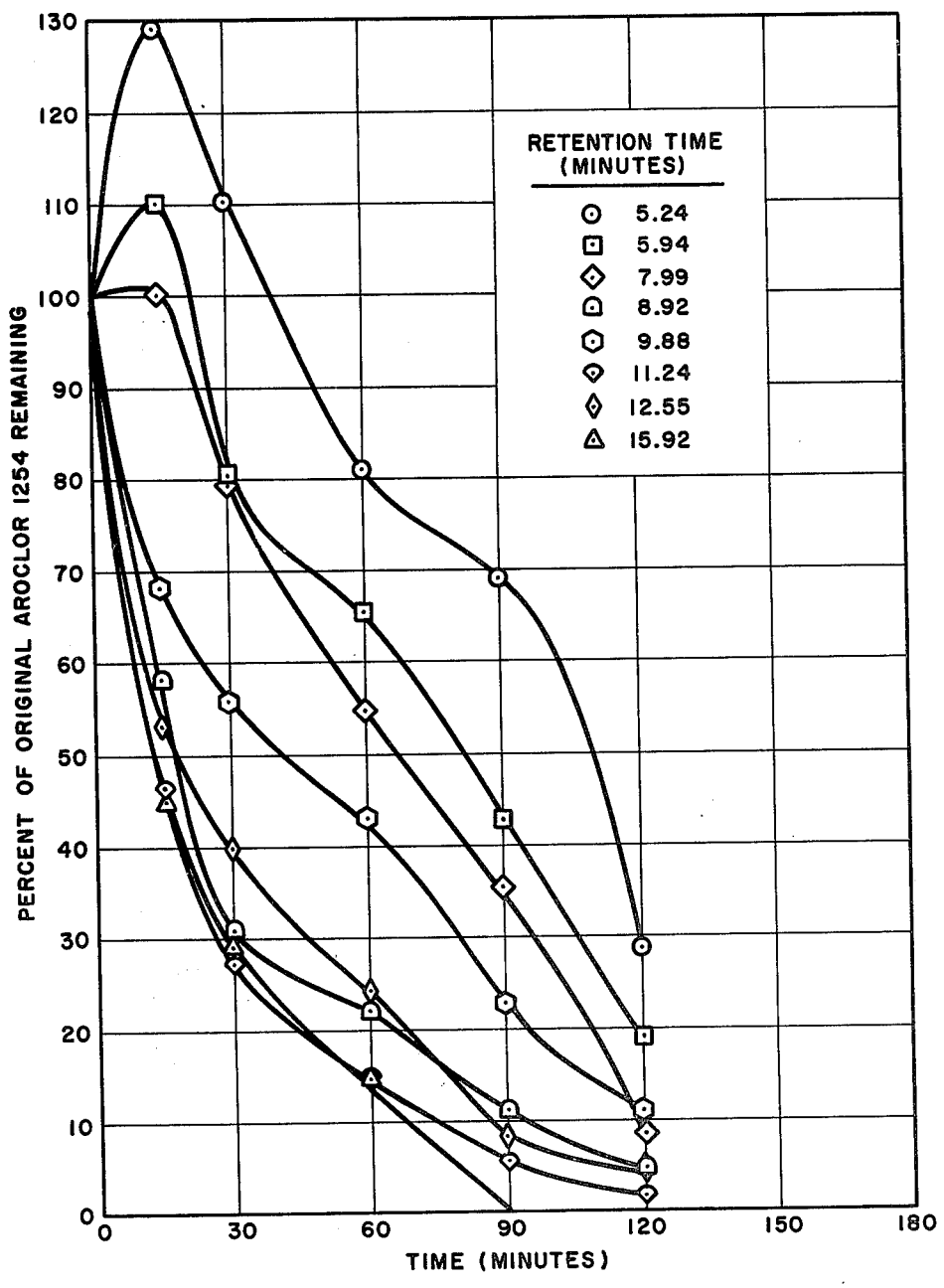
FIGS. 6, 7 and 8 show the percent degradation of the individual components of Aroclor 1254 by treatment with UV alone, UV plus $O_3$ and UV plus $H_2$ respectively.
Figure 7:
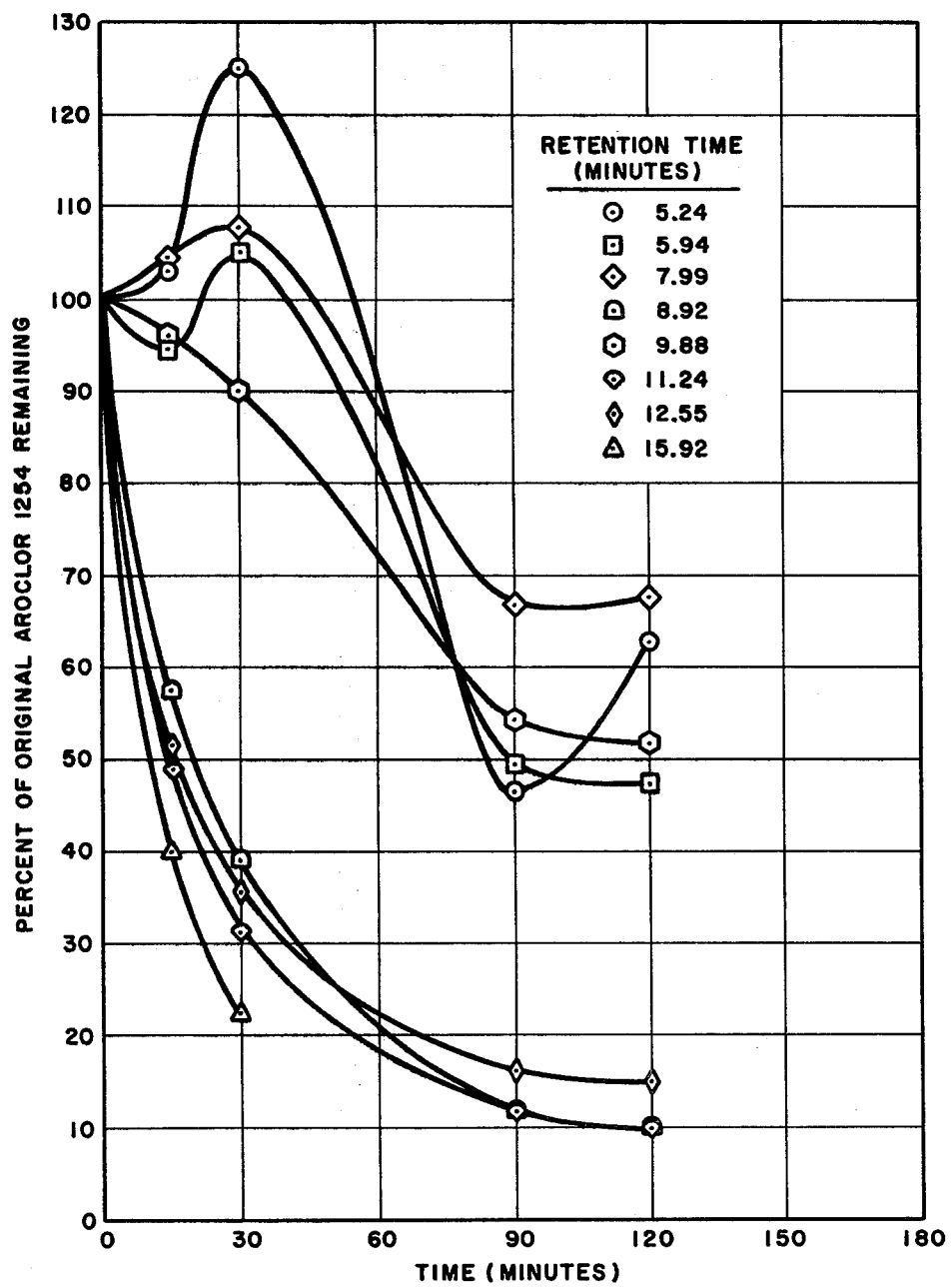
Figure 8:
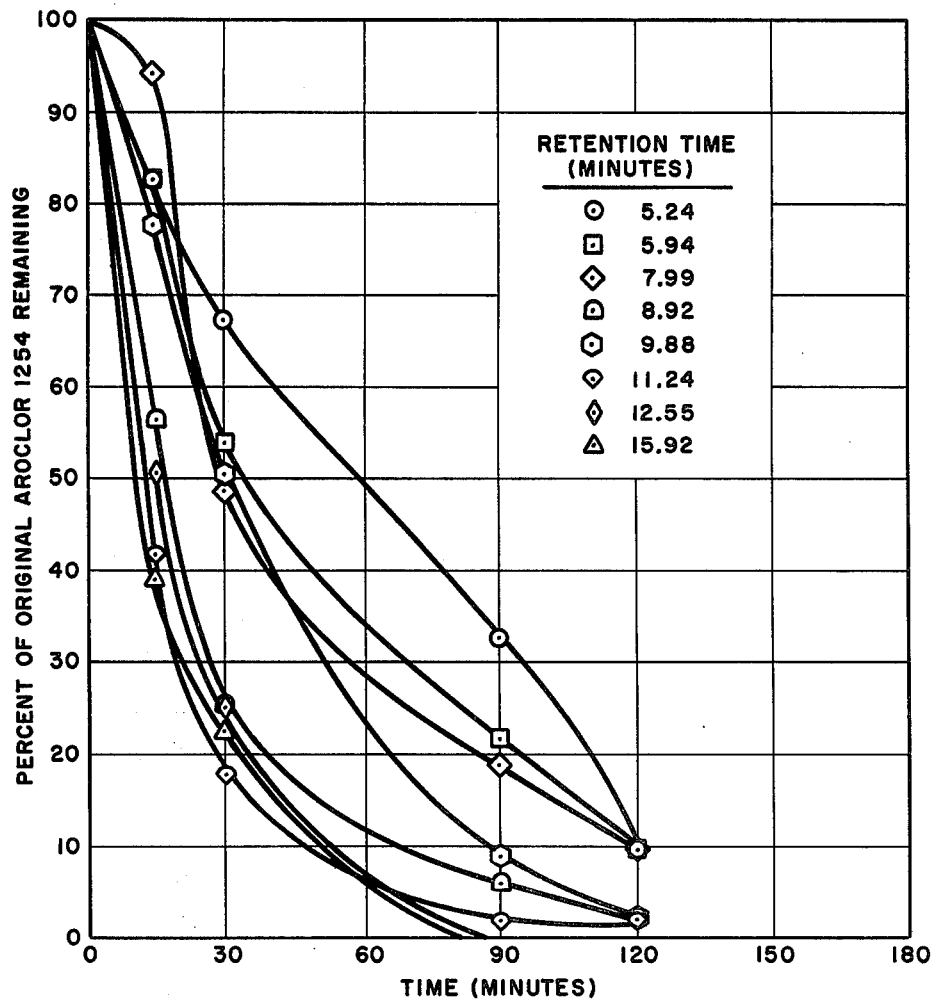

FIGS. 6-8 show the concentration of the individual chlorinated biphenyl components as a function of time for each treatment methodology. Retention time increases with the percentage of compound chlorine. Inspection of these figures shows the rapid degradation of the high chlorinated biphenyls (peaks 5-9) with all treatment methodologies. The lower chlorinated biphenyls disappear at a slower rate and even increase in concentration in the UV alone and UV plus $O_3$ treatments. These curves are consistent with known mechanisms for photodegradation of PCBs.

Table III shows the total final concentrations of all of the PCB components and their total % degradation at the end of two hours.

TABLE III

| Treatment | ppm Final Concentration | % Degradation |
|---|---|---|
| UV | 0.93 | 91.5 |
| UV + $H_2$ | 0.5 | 95 |
| UV + $O_3$ | 3.49 | 68 |

Tests of the stock solution treated with hydrogen gas only, showed that substantially none of the PCB was lost by volatilization. The degradation test results, in fact, show an increase in the more volatile components (low chlorinated species) which is indicative of photochemical reaction.

EXAMPLE III

Treatment of Tetrabromophthalic Anhydride (TBPA)

TBPA is a high melting white crystalline material which is insoluble in water and sparingly soluble in methanol. In basic methanol, e.g., methanol rendered alkaline with NaOH, the anhydride functional group is reactive, forming the sodium salts and the methyl esters.

A weighed amount of TBPA was dissolved in methanol alkalized to pH11 to make a 100 ppm stock solution. 1.5 l portions were treated with UV alone, UV and ozone at an ozone flow rate of 0.41 l/min., and UV and hydrogen at a hydrogen flow rate of 0.75 l/min. in the reactor aforedescribed. Samples of each treatment methodology were taken at 15, 30, 60, 90 and 120 minutes for analysis.

The analyses were made using a Waters high pressure liquid chromatograph with a 2537Å detector. The carrier solvent was methanol and the flow rate was 1 ml/min. Samples were injected into the LC without any pretreatment. The TBPA concentration of the treated samples was obtained by comparison to a standard curve.

Bromide ion concentrations were measured with an Orion bromide electrode. Samples were prepared by neutralizing 5 ml of each solution with Ultrex nitric acid. The resulting methanolic solution was evaporated to dryness and then diluted to 8 ml with distilled water. Bromide ion concentrations were calculated by comparison with a standard curve constructed from NaBR standards of known composition.

Figure 9:
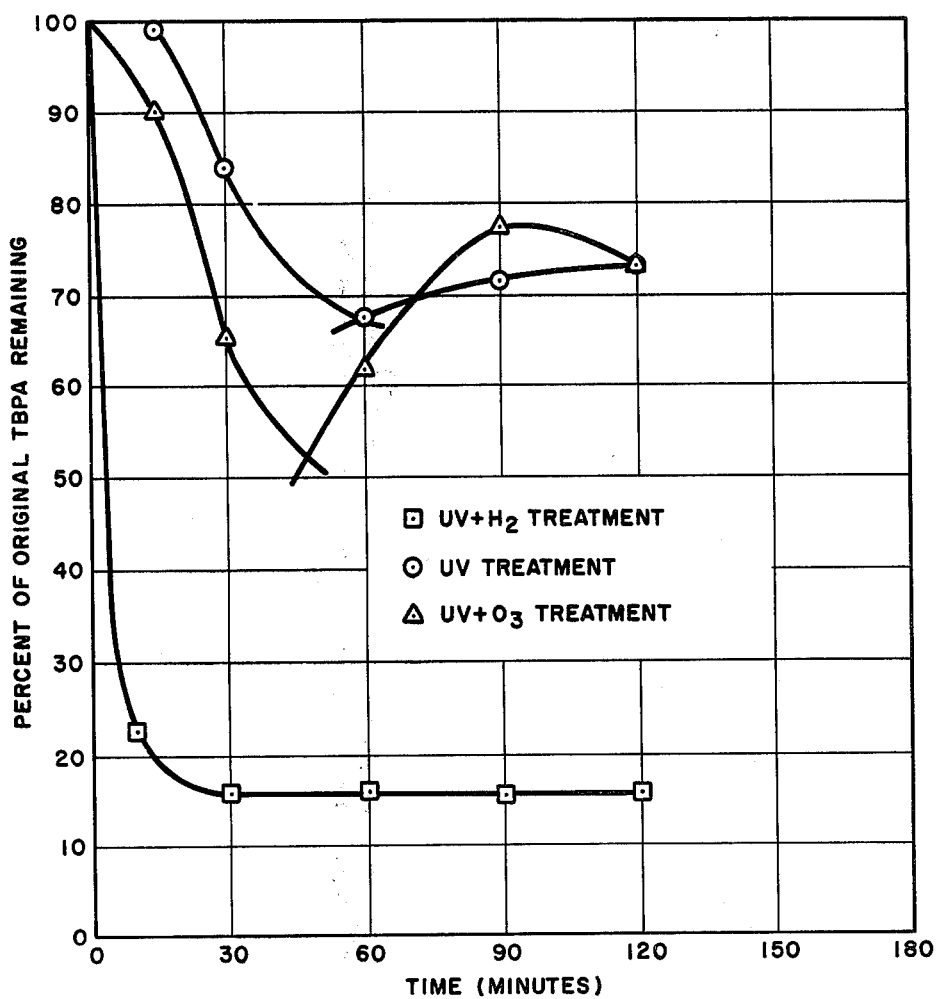
FIG. 9 shows the percent degradation of TBPA in basic methanol by treatment with UV alone, UV plus $O_3$, and UV plus $H_2$.
Figure 10:
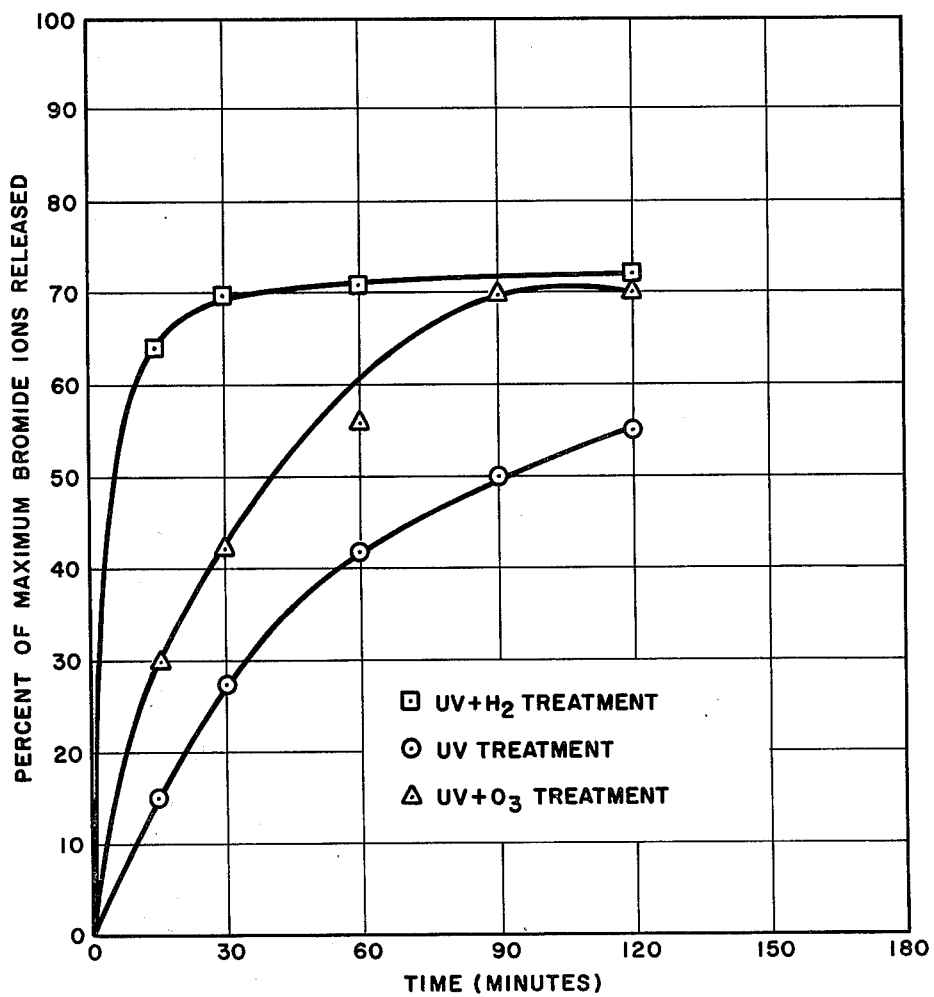
FIG. 10 shows the percent of maximum bromide ions released from TBPA using the three treatment methodologies.

The results obtained from the LC analysis of the TBPA concentration of the samples are presented in FIG. 9. The UV alone and UV plus $O_3$ data appear to be very erratic. This erratic appearance is due to the formation of decomposition product, probably the tri- or di-brominated product which is not separated from the original TBPA peak. FIG. 10 shows the comparative formation of Br ion as a function of time for the three methodologies and is a more accurate indication of debromination than in FIG. 9.

The bromide analysis correlates well with the LC analysis of TBPA when treated with UV plus $H_2$. Upon treatment with UV plus $H_2$, the TBPA is decomposed extremely rapidly during the first 15 minutes, after which TBPA degradation and bromide formation slow down. The lowest TBPA concentration ($\sim 16\%$ of the original) coupled with the highest bromide concentration obtained ($\sim 50$ ppm) indicate that the molecules were completely debrominated. An equilibrium is then established between the TBPA and the resultant phthalic anhydride. To debrominate the remaining TBPA, this equilibrium must be shifted.

Both the UV alone and the UV plus $O_3$ approach the three bromine removal level but at much slower rates. With these treatment methodologies, several other compounds also appear in significant quantities on the LC chromatograms. These substances did not appear in substantial quantities when the TBPA was treated with UV plus $H_2$.

Thus, the UV plus $H_2$ treatment in basic methanol not only results in significantly more rapid degradation of TBPA than UV alone or UV plus $O_3$ but in different decomposition products.

It is clearly apparent from all of the foregoing data that degradation of halogenated organic compounds by treatment with UV plus $H_2$, preferably in alkaline solution, provides an effective and economical means for removing such compounds from manufacturing effluent and/or the environment. It has also been shown that the treatment of such compounds with UV alone in aqueous alkaline solutions also provides significant degradation. By "UV alone", as used in the specification and claims, is meant treatment with ultraviolet radiation without additional chemical treatment other than the use of a solvent for the halogenated compound. The term "aqueous alkaline solution" means a solvent free from additional organic solvent.

Although this invention has been described with reference to illustrative embodiments thereof, it will be apparent to those skilled in the art that the principles of this invention can be embodied in other forms but within the scope of the claims.

I claim:

1. Process for reducing a halogenated organic compound having at least one carbon-halogen group in such manner as to remove halogen from said compound, comprising: treating said compound with ultraviolet radiation in the range of about 1800 to 4000Å and hydrogen in the absence of any substantial amount of oxidizing agent.

2. Process of claim 1 in which the compound has a plurality of carbon-halogen groups.

3. Process of claim 2 wherein the UV wavelength range is about 1800–2540Å.

4. Process of claim 2 in which the compound is in liquid solution.

5. Process of claim 4 wherein the UV wavelength range is about 1800–2540Å.

6. Process of claim 4 in which the solution comprises an organic solvent.

7. Process of claim 6 in which the compound is kepone.

8. Process of claim 6 in which the compound is polybrominated phthalic anhydride.

9. Process of claim 6 in which the compound is polyhalogenated biphenyl.

10. Process of claim 9 in which the polyhalogenated biphenyl is polychlorobiphenyl.

11. Process of claim 6 wherein the UV wavelength range is about 1800–2540Å.

12. Process of claim 11 in which the compound is kepone.

13. Process of claim 11 in which the compound is polybrominated phthalic anhydride.

14. Process of claim 11 in which the compound is polyhalogenated biphenyl.

15. Process of claim 14 in which the polyhalogenated biphenyl is polychlorobiphenyl.

16. Process of claim 6 in which the organic solvent is methanol.

17. Process of claim 16 in which the compound is kepone.

18. Process of claim 16 in which the compound is polybrominated phthalic anhydride.

19. Process of claim 16 in which the compound is polyhalogenated biphenyl.

20. Process of claim 19 in which the polyhalogenated biphenyl is polychlorobiphenyl.

21. Process of claim 16 wherein the UV wavelength range is about 1800–2540Å.

22. Process of claim 21 in which the compound is kepone.

23. Process of claim 21 in which the compound is polybrominated phthalic anhydride.

24. Process of claim 21 in which the compound is polyhalogenated biphenyl.

25. Process of claim 24 in which the polyhalogenated biphenyl is polychlorobiphenyl.

26. Process of claim 1 in which the compound is in liquid solution.

27. Process of claim 26 wherein the UV wavelength range is about 1800–2540Å.

28. Process of claim 3 in which the solution comprises an organic solvent.

29. Process of claim 28 wherein the UV wavelength range is about 1800–2540Å.

30. Process of claim 28 in which the organic solvent is methanol.

31. Process of claim 30 wherein the UV wavelength range is about 1800–2540Å.

32. Process of claim 1 wherein the UV wavelength range is about 1800–2540Å.

33. Process for degrading a halogenated organic compound having at least one carbon-halogen group in such manner as to remove halogen from said compound, said compound being of the type which forms alkali metal salts when treated with an aqueous alkaline solution containing sodium or potassium ions, comprising, dissolving said compound in a solvent comprising an aqueous alkaline solution containing sodium and/or potassium ions, said solution being substantially free from organic solvent, with ultraviolet radiation in the range of about 1800 to 4000Å substantially in the absence of other compound treating agent.

34. Process of claim 33 in which the compound has a plurality of carbon-halogen groups.

35. Process of claim 34 in which the ultraviolet wavelength range is about 1800–2540Å.

36. Process of claim 35 in which the compound is kepone.

37. Process of claim 34 in which the compound is kepone.

38. Process of claim 33 in which the solvent is a solution of sodium and/or potassium oxide and/or hydroxide.

39. Process of claim 38 in which the ultraviolet wavelength range is about 1800–2540Å.

40. Process of claim 39 in which the compound is kepone.

41. Process of claim 38 in which the compound is kepone.

42. Process of claim 33 in which the ultraviolet wavelength range is about 1800–2540Å.

43. Process of claim 42 in which the compound is kepone.

44. Process of claim 33 in which the compound is kepone.

45. Process for degrading a halogenated organic compound having at least one carbon-halogen group in such manner as to remove halogen from said compound, comprising: treating an alkaline liquid solution of said compound with ultraviolet radiation in the range of about 1800 to 4000 Å and hydrogen in the absence of any substantial amount of oxidizing agent.

46. Process of claim 45 in which alkalinity is produced by sodium and/or potassium oxide and/or hydroxide.

47. Process of claim 46 wherein the UV wavelength range is about 1800–2540Å.

48. Process of claim 40 in which the compound is of the type which forms alkali metal salts when treated with an aqueous alkaline solution containing sodium or potassium ions and the solvent comprises an aqueous alkaline solution containing sodium and/or potassium ions, said solution being substantially free from organic solvent.

49. Process of claim 48 wherein the UV wavelength range is about 1800–2540Å.

50. Process of claim 48 in which the compound has a plurality of carbon-halogen groups.

51. Process of claim 50 in which the compound is kepone.

52. Process of claim 50 in which the solvent comprises a solution of sodium and/or potassium oxide and/or hydroxide.

53. Process of claim 52 in which the compound is kepone.

54. Process of claim 52 wherein the UV wavelength range is about 1800–2540Å.

55. Process of claim 54 in which the compound is kepone.

56. Process of claim 50 wherein the UV wavelength range is about 1800–2540Å.

57. Process of claim 56 in which the compound is kepone.

58. Process of claim 48 in which the solvent comprises a solution of sodium and/or potassium oxide and/or hydroxide.

59. Process of claim 58 wherein the UV wavelength range is about 1800–2540Å.

60. Process of claim 45 wherein the UV wavelength range is about 1800–2540Å.

61. Process of claim 45 in which the compound has a plurality of carbon-halogen groups.

62. Process of claim 61 wherein the UV wavelength range is about 1800–2540Å.

63. Process of claim 61 in which alkalinity is produced by sodium and/or potassium oxide and/or hydroxide.

64. Process of claim 63 wherein the UV wavelength range is about 1800–2540Å.

65. Process of claim 61 in which the solution comprises an organic solvent.

66. Process of claim 65 in which the compound is kepone.

67. Process of claim 65 in which the compound is polybrominated phthalic anhydride.

68. Process of claim 65 in which the compound is polyhalogenated biphenyl.

69. Process of claim 68 in which the polyhalogenated biphenyl is polychlorobiphenyl.

70. Process of claim 65 in which alkalinity is produced by sodium and/or potassium oxide and/or hydroxide.

71. Process of claim 70 in which the compound is kepone.

72. Process of claim 70 in which the compound is polybrominated phthalic anhydride.

73. Process of claim 70 in which the compound is polyhalogenated biphenyl.

74. Process of claim 73 in which the polyhalogenated biphenyl is polychlorobiphenyl.

75. Process of claim 70 in which the organic solvent is methanol.

76. Process of claim 75 in which the compound is kepone.

77. Process of claim 75 in which the compound is polybrominated phthalic anhydride.

78. Process of claim 75 in which the compound is polyhalogenated biphenyl.

79. Process of claim 78 in which the polyhalogenated biphenyl is polychlorobiphenyl.

80. Process of claim 75 wherein the UV wavelength range is about 1800–2540Å.

81. Process of claim 80 in which the compound is kepone.

82. Process of claim 42 in which the compound is polybrominated phthalic anhydride.

83. Process of claim 80 in which the compound is polyhalogenated biphenyl.

84. Process of claim 83 in which the polyhalogenated biphenyl is polychlorobiphenyl.

85. Process of claim 70 wherein the UV wavelength range is about 1800–2540Å.

86. Process of claim 85 in which the compound is kepone.

87. Process of claim 85 in which the compound is polybrominated phthalic anhydride.

88. Process of claim 85 in which the compound is polyhalogenated biphenyl.

89. Process of claim 88 in which the polyhalogenated biphenyl is polychlorobiphenyl.

90. Process of claim 65 in which the organic solvent is methanol.

91. Process of claim 90 in which the compound is kepone.

92. Process of claim 90 in which the compound is polybrominated phthalic anhydride.

93. Process of claim 90 in which the compound is polyhalogenated biphenyl.

94. Process of claim 93 in which the polyhalogenated biphenyl is polychlorobiphenyl.

95. Process of claim 90 wherein the UV wavelength range is about 1800–2540Å.

96. Process of claim 95 in which the compound is kepone.

97. Process of claim 95 in which the compound is polybrominated phthalic anhydride.

98. Process of claim 95 in which the compound is polyhalogenated biphenyl.

99. Process of claim 98 in which the polyhalogenated biphenyl is polychlorobiphenyl.

100. Process of claim 65 wherein the UV wavelength range is about 1800–2540Å.

101. Process of claim 100 in which the compound is kepone.

102. Process of claim 100 in which the compound is polybrominated phthalic anhydride.

103. Process of claim 100 in which the compound is polyhalogenated biphenyl.

104. Process of claim 103 in which the polyhalogenated biphenyl is polychlorobiphenyl.

105. Process of claim 45 in which the solution comprises an organic solvent.

106. Process of claim 105 wherein the UV wavelength range is about 1800–2540Å.

107. Process of claim 105 in which the organic solvent is methanol.

108. Process of claim 107 wherein the UV wavelength range is about 1800–2540Å.

109. Process of claim 105 in which alkalinity is produced by sodium and/or potassium oxide and/or hydroxide.

110. Process of claim 109 wherein the UV wavelength range is about 1800–2540Å.

111. Process of claim 109 in which the organic solvent is methanol.

112. Process of claim 111 wherein the UV wavelength range is about 1800–2540Å.

* * * * *

UNITED STATES PATENT AND TRADEMARK OFFICE
CERTIFICATE OF CORRECTION

PATENT NO. : 4,144,152

DATED : March 13, 1979

INVENTOR(S) : Judith A.F. Kitchens

It is certified that error appears in the above-identified patent and that said Letters Patent are hereby corrected as shown below:

Columns 5: Table I, under heading "Sample Conditions", four occurrences, cancel "Ag" and substitute Aq .

Column 5 line 58; after "one-half" cancel "and" and substitute by.

Claim 48, line 1, cancel "40" and substitute 45.

Claim 82, line 1, cancel "42" and substitute 80.

*Signed and Sealed this*

*Fourth* Day of *March 1980*

[SEAL]

Attest:

SIDNEY A. DIAMOND

*Attesting Officer*    *Commissioner of Patents and Trademarks*